United States Patent [19]

Shu

[11] Patent Number: 5,314,467
[45] Date of Patent: May 24, 1994

[54] COMPOSITE CURVATURE BILEAFLET PROSTHETIC HEART VALVE WITH SERPENTINE CURVE HINGE RECESSES

[75] Inventor: Mark C. S. Shu, Brooklyn Park, Minn.

[73] Assignee: Medtronic, Inc., Minneapolis, Minn.

[21] Appl. No.: 932,110

[22] Filed: Aug. 19, 1992

Related U.S. Application Data

[63] Continuation-in-part of Ser. No. 711,244, Jun. 6, 1991, abandoned.

[51] Int. Cl.⁵ .................. A61F 2/24; F16K 15/00; F16K 17/00; F16K 21/04
[52] U.S. Cl. .................................. 623/2; 137/521; 137/527
[58] Field of Search ................ 623/2; 137/521, 527

[56] References Cited

U.S. PATENT DOCUMENTS

| | | | |
|---|---|---|---|
| 4,308,624 | 1/1982 | Klanitter | 623/2 |
| 4,689,046 | 8/1987 | Bokros | 623/2 |
| 4,863,467 | 9/1989 | Bokros | 623/2 |
| 4,872,875 | 10/1989 | Hwang | 623/2 |
| 4,888,010 | 12/1989 | Bokros | 623/2 |
| 5,080,669 | 1/1992 | Tascon et al. | 623/2 |

FOREIGN PATENT DOCUMENTS 8802247  4/1988  World Int. Prop. O. ............ 623/2

*Primary Examiner*—Randall L. Green
*Assistant Examiner*—Dinh X. Nguyen
*Attorney, Agent, or Firm*—Reed A. Duthler; Harold R. Patton

[57] ABSTRACT

A heart valve prosthesis having an annular valve housing or base and two leaflets supported for pivotable movement within the annular valve housing. Each valve leaflet possesses a composite curvature shape with pivoting hinges being purposely offset to the hydraulic force center of the annular valve housing to provide fast response of the leaflets to flow direction change. The hinge mechanism includes modified serpentine curved hinge recesses in the annular valve housing for receiving elongated leaflet ears allowing the leaflets to change their motion modes approaching the closed position to reduce leaflet-edge tangential velocity and impact of the minor edges against one another and the major edges against the housing seat upon closure. The composite curvature leaflets allow maximal central flow with consequent lower pressure drop during the open phase and minimal regurgitation during the closing phase. The curved leaflet major trailing edges in the open position reduces boundary separation and associated turbulence along the flow stream direction.

13 Claims, 12 Drawing Sheets

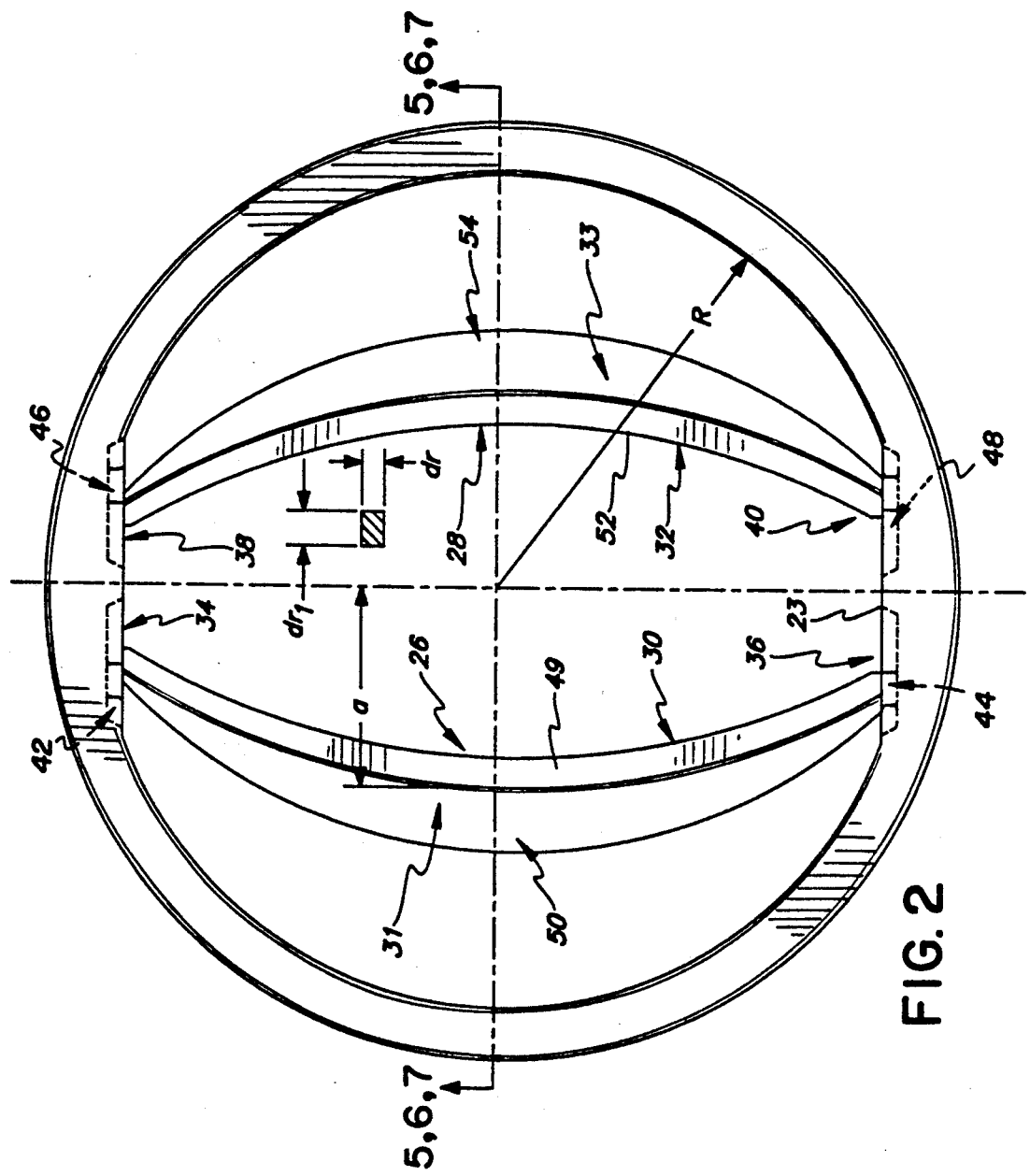

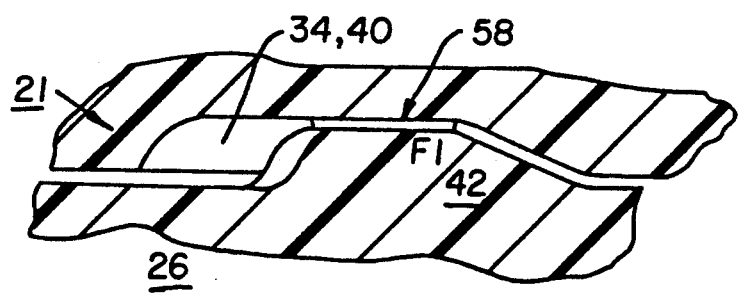
FIG. 4B
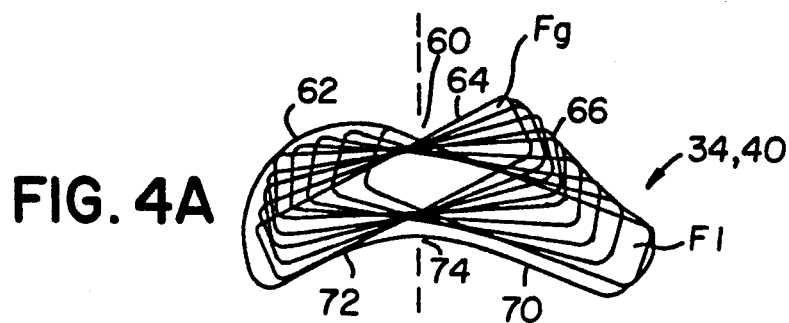
FIG. 4A
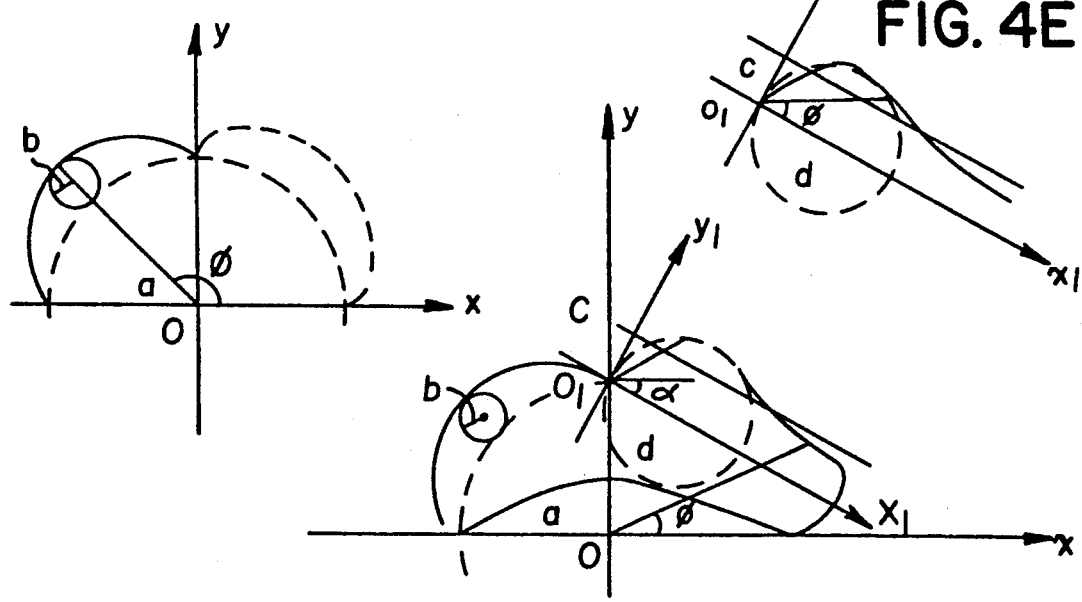
FIG. 4D
FIG. 4E
FIG. 4C
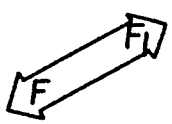

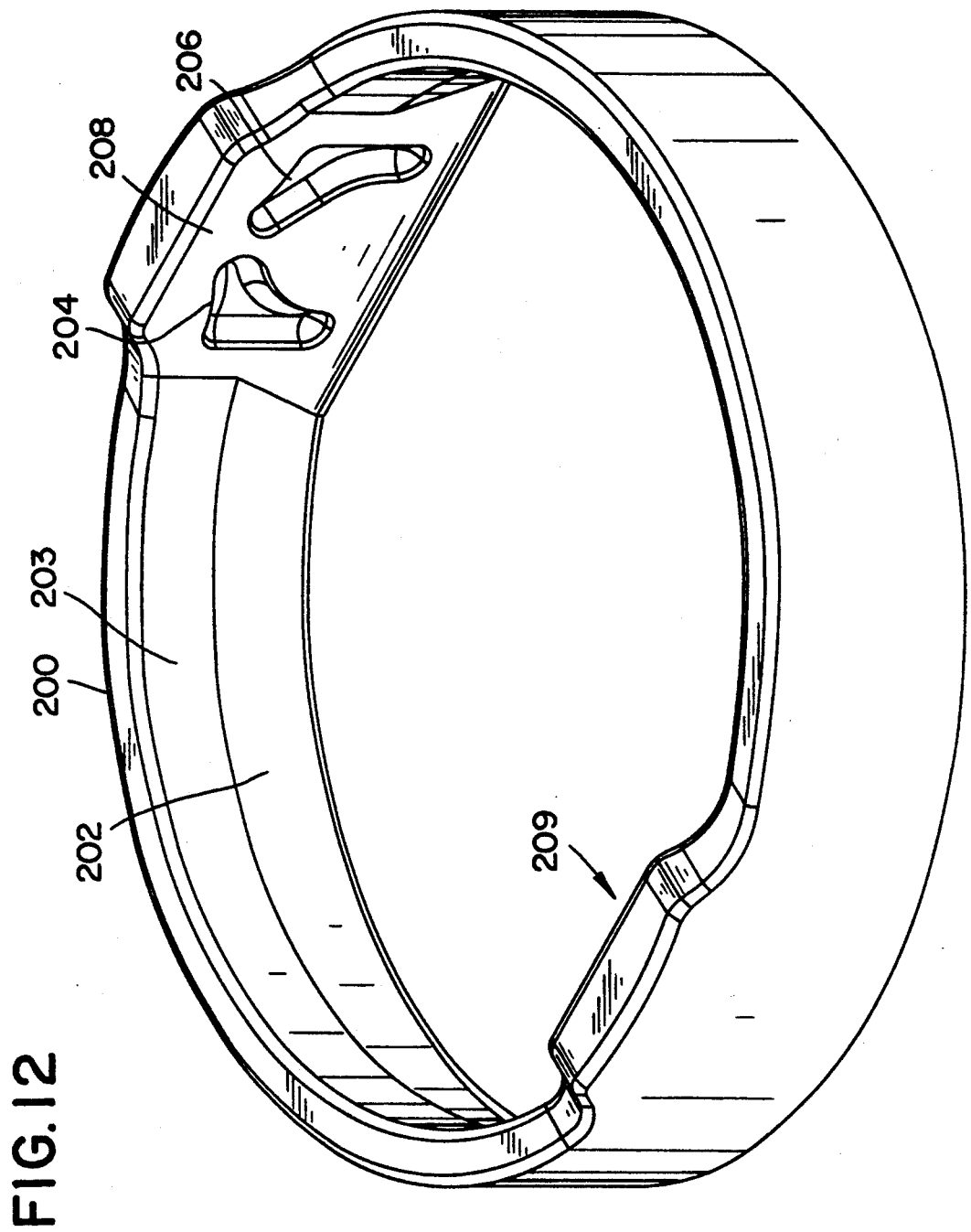

COMPOSITE CURVATURE BILEAFLET PROSTHETIC HEART VALVE WITH SERPENTINE CURVE HINGE RECESSES

This is a continuation-in-part of copending application(s) Ser. No. 07/711,244 filed on Jun. 6, 1991 now abandoned.

BACKGROUND OF THE INVENTION

The present invention relates to heart valve prostheses generally and more particularly relates to mechanical bileaflet prosthetic heart valves.

Heart valve prostheses are well known in the art. Generally speaking, heart valve prostheses can be classified in two major types or categories. One type of prosthesis employs a tissue valve of animal (usually porcine) origin in its blood flow regulating valve mechanism. The other type of heart valve prosthesis utilizes a ball, a disc, valve leaflets or other mechanical devices to regulate the direction of blood flow through the prosthesis. The latter type of prosthesis is usually known in the art as "mechanical" heart valve prosthesis. For specific examples and detailed descriptions of the heart valve prostheses of the prior art, reference is made to U.S. Pat. Nos. 3,744,062; 3,835,475; 3,997,923; 4,364,126 and 4,106,129.

By their very nature, the mechanical heart valve prostheses have metal or plastic surfaces which, when exposed to the blood flow, are thrombogenic to some degree related to deficiencies in design, physical structure, operational characteristics and structural material. In more recent years, pyrolytic carbon coated bileaflet heart valves having flat leaflets of the type shown in U.S. Pat. Nos. 4,276,658; Re. 31,040; 4,935,030; 4,863,458; 4,822,353; 4,888,010; 4,272,854; 4,451,937; 4,689,046; and 4,863,467, as well as PCT Publication No. WO89/00841, have been published. Other prosthetic heart valves of the type shown in U.S. Pat. Nos. 4,484,365, 4,950,287 and 4,863,459, disclose leaflets curved in the downstream direction. A further group of designs employing conical or cylindrical surface leaflets and pivot axes adjacent to or somewhat displaced from the center of the valve wherein the leaflets typically open away from the center of the valve to provide for central blood flow are disclosed in U.S. Pat. Nos. 4,808,180; 4,363,142; 4,274,437; 4,446,577; 4,328,592; 4,308,624; 4,443,894; 4,357,715; 4,308,624; 4,488,318; and 4,676,789.

Such heart valve designs having a variety of shapes of the leaflets and configurations of hinges have been developed in an effort to improve reliability, hemodynamics, ease of surgical implantation, and the reduction or elimination of the development of thrombi.

However, some of the prior art heart valve prostheses have designs which are functionally inefficient and resistive to the free passage of blood. Others cause blood stagnation points or regions and turbulence which results in the formation of blood clots on the valve structure to obstruct the normal leaflet movement. Hemolysis (destruction of blood elements) is still a concern in prior art valves that have fast closing contact speed and momentum by which blood elements are mechanically crushed.

In prior designs, considerable attention has been paid to the hinge mechanisms and particular shapes of the bileaflet valves in an effort to improve the blood flow characteristics through the valve orifice in its open position, to reduce the pressure drop and turbulence caused by the profiles of the leaflets to flowing blood. Designs intended to reduce noise of closure of the leaflets, and to provide for continuous cleaning of the valve surfaces and wiping of the hinges have also been advanced in the listed patents. The above listed patents depict various hinge mechanisms that provide rotation and in certain instances, translation of the leaflets during the opening and closing phases. However, most of these designs have never been utilized due to a variety of design shortcomings listed above.

In this regard, to avoid clotting of blood, it is desirable to make further improvements in mechanical heart valve prostheses with regard to these characteristics as well as with regard to simplicity and cost of construction, reliability of operation, and reduction of thrombogenecity. The mechanical heart valve of the present invention provides such improvements.

SUMMARY OF THE INVENTION

It is an object of the present invention to provide a mechanical heart valve prosthesis which has a low profile and a bileaflet design which allows a large central orifice area to obtain optimal central flow characteristics.

It is another object of the present invention to provide a mechanical bileaflet prosthetic heart valve with composite curvature leaflets for eliminating boundary separation and associated turbulence along the blood flow stream direction. It is still another object of the present invention to provide a bileaflet prosthetic heart valve having a modified serpentine curve hinge pivot mechanism to reduce the leaflet edge's tangential velocity near the closed position during the valve closing phase and hence reduce the impact of the leaflet edges against the annular housing and against each other on contact.

It is yet another object of the present invention to provide a bileaflet prosthetic heart valve with modified outflow section of the annular valve housing to eliminate leaflet impingement tendency.

It is a further object of the present invention to provide a moving leaflet heart valve hinge which provides for controlled rotation and translation of the valve leaflet(s) in the direction of blood flow during opening and closing, whereby the valve leaflet(s) accelerate and decelerate in a controlled fashion and the contacting surfaces of the hinge mechanism wipe one another so as to minimize blood clot formation in the region of the hinge mechanism.

It is still a further object of the present invention to provide a prosthetic heart valve that meets the above stated objectives, is reliable in use and is simple and inexpensive to manufacture.

The foregoing objects and advantages are attained by a mechanical heart valve prosthesis having an annular base defining a blood passageway and a pair of valve leaflets which are mounted through a hinge mechanism for closing and opening the passageway for blood flow wherein the valve leaflets possess a composite curvature shape for eliminating boundary separation and associated turbulence of blood and are mounted through a hinge mechanism to the annular base so as to allow the leaflets to change their motion mode near the closed position to reduce leaflet edge tangential velocity upon approaching closure.

The bileaflet prosthetic heart valve with composite curvature leaflets and a special hinge mechanism provides a maximal proportion of blood flow through the central opening defined by the interior facing surfaces of the leaflets in their open phase in comparison to the peripheral blood flow between the interior surface of the annular valve body and the opposite surfaces of the leaflets.

In accordance with the present invention, the preferred hinge mechanism is effected by a pair of elongated ear members formed on and by opposite sides of each valve leaflet at points purposely offset to hydraulic force center for providing a fast initial response of the leaflets to blood flow direction change. The elongated ear members are fitted into hinge point recesses in the interior surface of the annular base wherein each hinge recess provides an open recess position, a closed recess position, and a torque center cam for controlling the acceleration and deceleration of the leaflets as the elongated ear member bears against the torque center cam as blood flow change of direction swings the leaflets between their open and closed positions.

During operation of the mechanical valve prosthesis, the valve leaflets undergo limited axial and radial translational movement limited by the contact of the ends of the elongated ears against the recess walls. The contact of the ends of the elongated ears against the recess walls guides the movements of the valve leaflets to accomplish to successive rotation and translation in the valve closing phase. The final contact motion of the valve leaflet edges against the annular base housing and against each other is completed by translation which causes soft closing of the major edges against the seat formed at an angle to the interior surface of the annular base. Lower valve closing noise and enhanced fatigue life of the valve are expected by this design.

BRIEF DESCRIPTION OF THE DRAWINGS

The features of the present invention can be best understood, together with further objects and advantages thereof, by reference to the following description taken together with the appended drawings in which:

FIG. 2 is an inflow view of one embodiment of a mechanical heart valve prostheses according to the present invention, depicting the composite curvature leaflets in the open position;

FIGS. 4A-4E are representations of the shape of the leaflet ear with respect to the shape of the hinge recess in the embodiment illustrated in FIG. 2 and provide illustrations of the geometric expression of the generation of the modified serpentine-epicycloid curve hinge recess employed therein;

FIG. 12 is a perspective view of the valve housing of a further embodiment of a valve according to the present invention;

DESCRIPTION OF THE PREFERRED EMBODIMENTS

Figure 1:
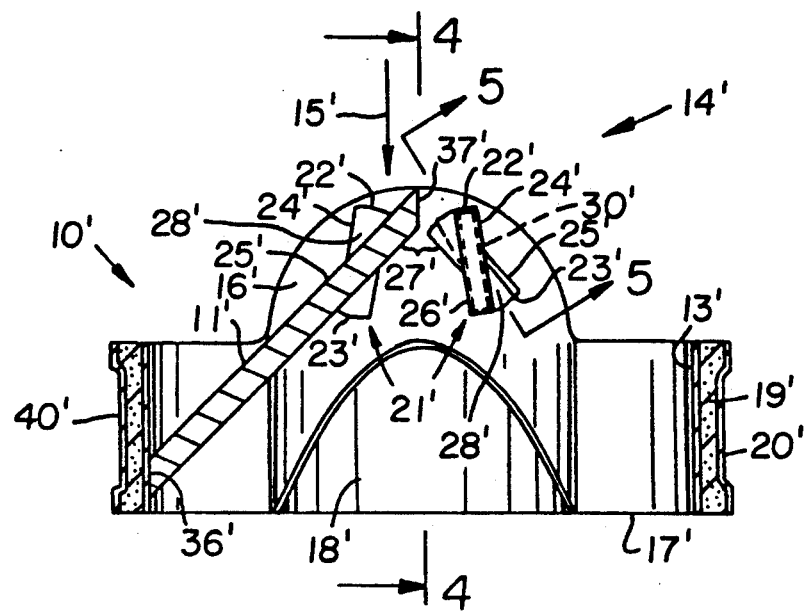
FIG. 1 is a sectional view of an embodiment of a prior art heart valve design showing the left-hand leaflet in the closed position and the shape of the hinge recess without the right-hand leaflet in place.

The following specification taken in conjunction with the drawing FIGS. 2-15 sets forth the preferred embodiments of the best mode contemplated by the inventor for carrying out his invention, although it should be understood that modifications can be accomplished within the scope of the present invention.

Figure 3:
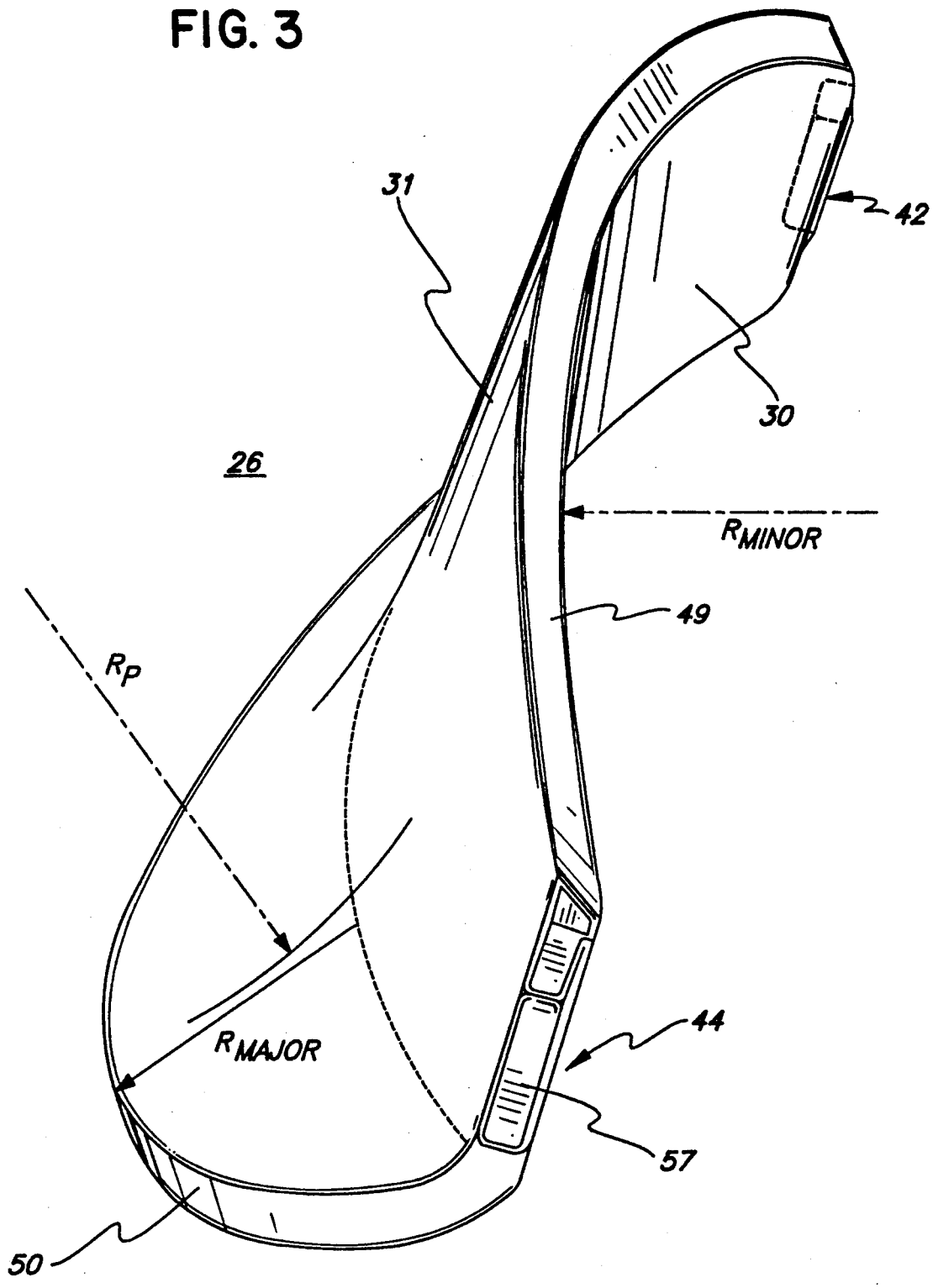
FIG. 3 is a perspective view of a one embodiment of a composite curvature leaflet according to the present invention.

Referring now to the drawing figures, and particularly to FIG. 1, it depicts FIG. 3 of the '658 patent listed above in order to illustrate the hinge mechanism of a widely implanted prior art bileaflet heart valve prosthesis. The element numerals from FIG. 3 of the '658 patent are hyphenated in FIG. 1, but otherwise find correspondence in the text of the '658 patent. The prior art heart valve of FIG. 1 is formed of a base 10' and leaflets 11' and 12' (not shown). The base 10' is a generally annular member whose inner wall 13' defines the blood passageway. The blood passageway is alternately opened and closed by movement of the leaflets 11' and 12' in response to the flow of blood. The base is provided with projections 14' having retaining means which cooperate with ears carried by the leaflets 11' and 12' to allow a pivotal movement of the leaflets between the open and closed positions.

The arrow 15' indicates the desired blood flow direction. As illustrated in FIG. 1, the projection 14' extends from the annular portion of base 10' in the upstream direction The inner face of the projection 14' is provided with a flat portion 16' while the outlet or downstream terminus 17' of base 10' is generally circular, the portion 18' providing a transition between the circular configuration of the outlet 17' and the flat portion 16'. As is known in the prior art, pyrolytic carbon is coated on a substrate, the reference numeral 19' indicating the substrate throughout the figures while the pyrolytic carbon coating is indicated at 20'.

Flat portion 16' of projection 14' is provided with retaining means generally designated at 21'. The retaining means 21' are formed as recesses within the flat 16' having opposing arcuate ends 22' and 23' joined by side walls 24'-27', to form a bearing surface 28'. As will be discussed more fully below, bearing surface 28' is a surface of revolution and preferably a spherical polygon. Except for their orientation within the flat 16', the retaining means 21' are identical.

The recesses which form the retaining means 21' may be formed by a cylindrical grinding wheel having the diameter desired for the bearing surface 28' by feeding the grinding wheel into the flat 16' to the desired depth thereby forming the side walls 24' and 26'. Such a grinding wheel (as well as the closed ear position of leaflet 12') is illustrated in phantom at 30'. The grinding wheel may then be swept through the arc defined by the ends 22'-23' to form the bearing surface 28' and the side walls 25' and 27'. Leaflets 11' and 12' are provided with ears which are adapted to extend into the recesses forming retaining means 21' for pivotal movement therein. Any or all of the side walls 24'-27' may be adapted to serve as stops for the leaflets 11' and 12' as by limiting motion of the leaflet ears within the retaining means 21. That is, as illustrated in FIG. 1, the side walls 25' and/or 27' may be position to prevent movement of the leaflet 11' past the illustrated position. An additional stop in the closed position is provided by engagement of the leaflet 11' with the inner face 13' of base 10' as further illustrated in FIG. 1. At least one of side walls 24' and 26' serve as a stop for the occluders 11' and 12' in the open position.

The configuration of the surface 28' and its cooperation with the projections or ears of the leaflets 11' and 12' is described in the '658 patent such that the perimeter or terminus of the ear is shaped as the section of a sphere having a diameter closely approximating, but slightly smaller than, the diameter of the surface 28'. In this manner, portions of the perimeter of the ear engage surface 28' during movement of the leaflets 11' and 12' between the open and closed position to maintain the leaflets in position retained by the side walls 24' and 26' and the end walls 22' and 23'. In other figures of the '658 patent, such as FIG. 5, it may be seen that there is very little if any play which would allow translational movement of the leaflets 11' and 12' in conjunction with their pivoting rotational movement between the open and closed positions. Consequently, as blood flow in the direction of the arrow 15' exerts a force against the closed leaflets 11', 12', they will swing open rapidly and shift from the position depicted with respect to the leaflet 11' to the phantom position 30'. The side walls 24' and 26' absorb the shock as the leaflets swing open to their full open position. Similarly, in pivoting from the open position to the closed position in response to a reversal of blood flow from the direction of the arrow 15', the leaflet ears rotate rapidly, gaining acceleration all of the way until the leaflet ears bear against the walls 27' and 25' and the minor edges 37' of the leaflets 11', 12' strike one another while the major edges 36, of the leaflets 11', 12' strike the inner wall 13' of the base 10'.

Figure 11A:
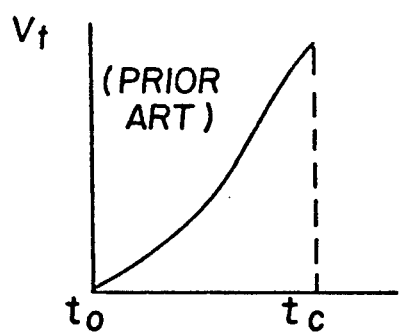
FIGS. 11A and 11B are graphical depictions of the acceleration and deceleration characteristics of the leaflets of a prior art heart valve design and the embodiment of the present invention illustrated in FIG. 2, respectively.
Figure 11B:
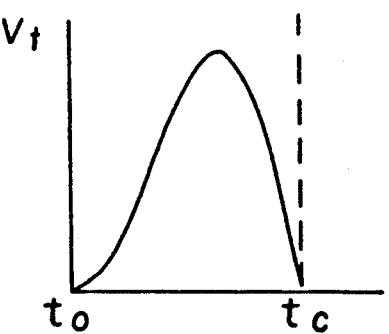

FIG. 11A illustrates the edge tangential velocity of the valve leaflets 11', 12' of the FIG. 1 type prior art heart valve between the time $t_o$ and the time $t_c$ which reflects the time elapsed for the leaflets 11', 12' to rotate from the open to the closed position. FIG. 11B illustrates the leaflet edge tangential velocity associated with the translation, rotation and translation (with slight continued rotation) afforded by the hinge mechanism of the present invention in moving from the open to the closed position, to be described hereafter.

The prior art valve leaflet of FIG. 1 is a flat leaflet and reference is made to FIG. 18 of the above-listed '592 patent which depicts a curved leaflet design employing a butterfly-shaped hinge mechanism similar to the above-described '658 patent hinge mechanism but apparently allowing for some degree of radial translation of the leaflets between the open and closed positions given the apparently shorter ear length than recess length. The '592 patent also depicts elongated recesses and spherical ears as well as pie-shaped recesses with elongated ears in further figures. In all embodiments of the '592 patent, therefore, a certain degree of rotational and translational motion is afforded but it is dependent not on the outline of the recess and matching leaflet ear but rather by the forces acting on the leaflets as they move from the open to closed positions and from the closed to the open positions.

The curvature of the '592 patent leaflets is properly that of a part of an ellipse formed by a plane cutting a right circular cylinder at an angle of about ten degrees to about twenty degrees as described in the '592 patent. This and other prior art valve designs are improved upon in the context of the present invention and the specific embodiments disclosed hereinafter.

The preferred embodiments of the present invention are depicted in FIGS. 2-15. The first embodiment employs the composite curvature leaflets and hinge mechanism of the present invention although somewhat differing leaflet designs that provide different ratios of central orifice open and blood flow to total peripheral orifice area and blood flow and differing profiles in the open and closed position may be desirable in differing sized aortic and mitral valve applications. The second embodiment employs flat leaflets with the modified serpertine-epicycloid curve hinge recess and elongated leaflet ears also employed in the first embodiment. The third embodiment employs a modified hinge recess having straight and serpentine guide walls and leaflet ears having rounded ends.

Turning to FIG. 2, the heart valve prosthesis illustrated includes an annular valve base 20 having inner and outer surfaces 22 and 24 and first and second leaflets 26 and 28 shown in the open position and in the direction of blood flow. Although not specifically shown, it will be understood that the outer surface 24 may contact a further reinforcing metal ring and conventional sewing ring of the type shown, for example, in the Medtronic U.S. Pat. No. 4,935,030 incorporated herein by reference. As is well known in the art, the annular valve base and its associated leaflets, reinforcing ring and sewing ring, may be provided in a variety of sizes to accommodate patients of varying ages and body sizes. The dimensions of the heart valve prosthesis also depend on whether the prosthesis is used in implantations replacing mitral, aortic or tricuspid heart valves. As is well known in the art, the sewing ring is affixed by sutures (not shown) to the living tissue (not shown) when the heart valve prosthesis is implanted.

Figure 8:
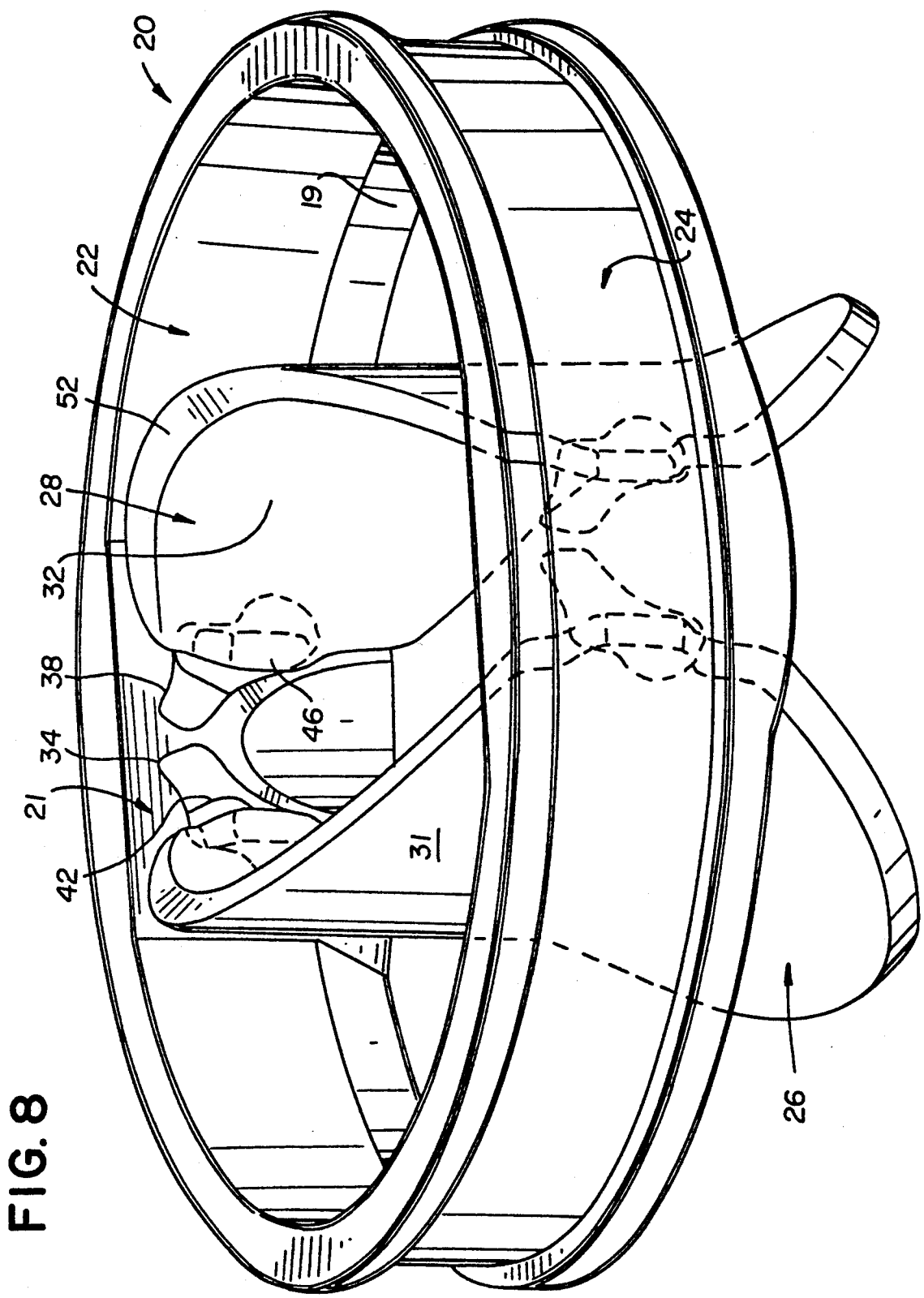
FIG. 8 is a perspective view of the embodiment of the present invention illustrated in FIG. 2 depicting the composite curvature leaflets in the open position.
Figure 9:
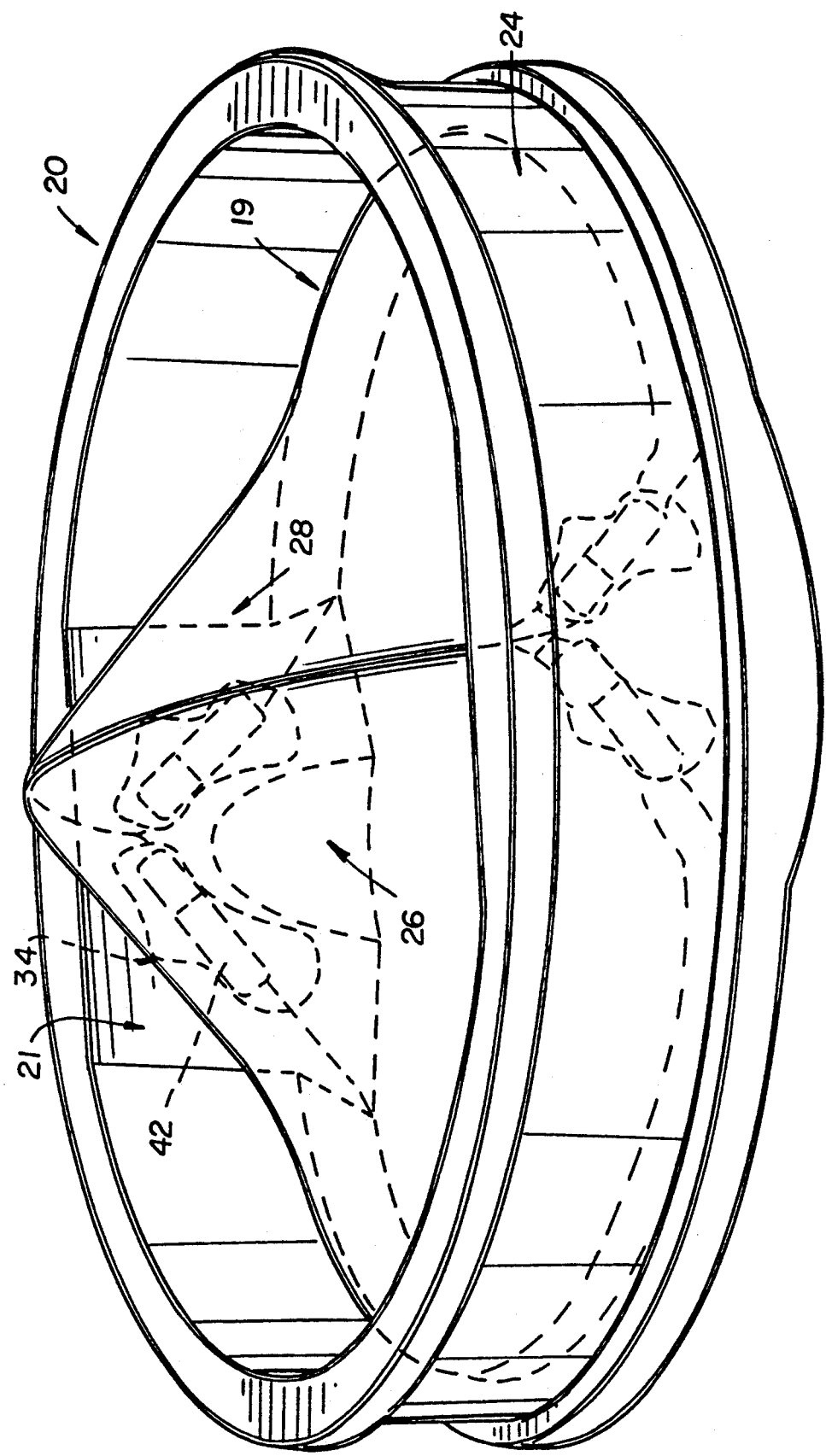
FIG. 9 is a perspective view of the embodiment of the present invention illustrated in FIG. 2 depicting the composite curvature leaflets in the closed position.

Returning to FIG. 2 valve leaflets 26 and 28 having inner surfaces 30 and 32, and outer surfaces 31 and 33, respectively, are mounted into four recesses 34, 36, 38, 40 at hinge points defined by leaflet ears 42, 44, 46 and 48 so that the valve leaflets may swing from the open position depicted in FIG. 8 to the closed position depicted in FIG. 9.

Each valve leaflet possesses a composite curvature shape curved to present minor and major edges 49 and 50, respectively, of the leaflet 26 (depicted in FIG. 3) and 52 and 54, respectively, of the leaflet 28. When the leaflets are closed as depicted in FIGS. 7 and 9, the major edges 50 and 54 seat against the inner seat surface 19 of the annular valve base 20 (shown in FIGS. 5–7) and the minor edges 48, 52 seat against one another.

During the open phase and in the open position, blood flows through the central orifice of the heart valve prosthesis defined by the facing inner surfaces 30, 32 of the leaflets 26 and 28 and through the outer orifices defined by the outer surfaces 31, 33 of the leaflets 26 and 28 and the inner surface 22 of the annular valve base 24. The ratio of the central orifice area to the total orifice area of the embodiment depicted in FIGS. 2–9 is approximately fifty percent. However, the volumetric blood flow through the central orifice is approximately seventy percent or more due to fluid flow effects along the surfaces 22 of base 20 and outer surfaces 31 and 33 of the leaflets 26 and 28. The blood washing action of the blood flow in the direction depicted in FIGS. 5–7 passes over the inner and outer surfaces 30, 32 and 31, 33 of the leaflets 26 and 28 and the inner surface 22 of the annular valve base 20.

The composite curvature of the valve leaflets is depicted in FIGS. 3 and 5–9. The radius of curvature $R_P$ of the inner and outer surfaces 30, 32 and 31, 33 extending from the major edges 50, 54 a distance toward the minor edges 49, 52 eliminates boundary separation and associated turbulence of the blood passing through the central and peripheral orifices in the open phase depicted in FIGS. 2, 5 and 8. It is generally desirable to have a central orifice area in the range of or greater than fifty percent of the total orifice area, but to have sufficient blood washing function along the circumferential interior surface 22 of the body 20 and the surfaces 31 and 33 of the leaflets 26 and 28 while minimizing pressure drop. Pressure drop is also minimized in the preferred embodiments of the present invention by providing the hinge point mechanism which allows the leaflets 26 and 28 to open to be virtually parallel to the blood flow (except along the major edges 50, 54 where the composite curvature afforded by radii $R_P$ and $R_{Major}$ is emphasized).

The radii of curvature of the major edges 50, 54 and the minor edges 49, 52 are represented by the arrows $R_{Major}$ and $R_{Minor}$. The radius of curvature $R_P$ is generally perpendicular or transfers to the other radii of the composite leaflet curvature.

Figure 5:
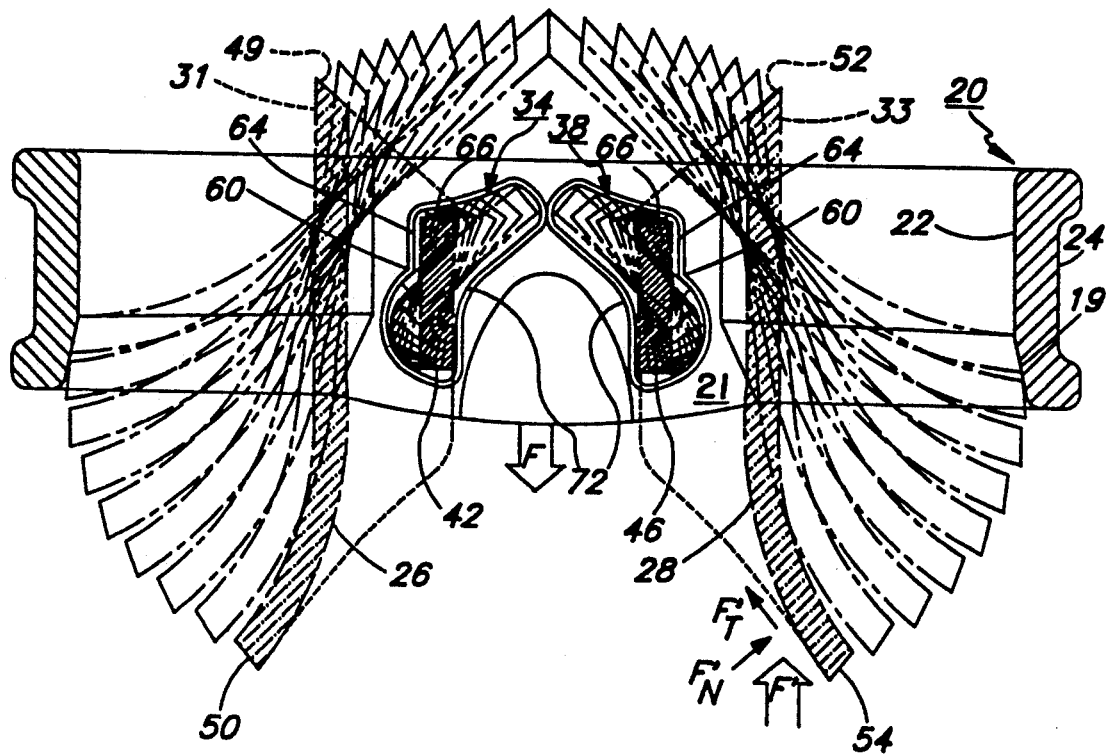
FIG. 5 is a cross-sectional view of the embodiment of the present invention illustrated in FIG. 2 taken along lines A—A of FIG. 2 with the valve leaflets in the open position.
Figure 6:
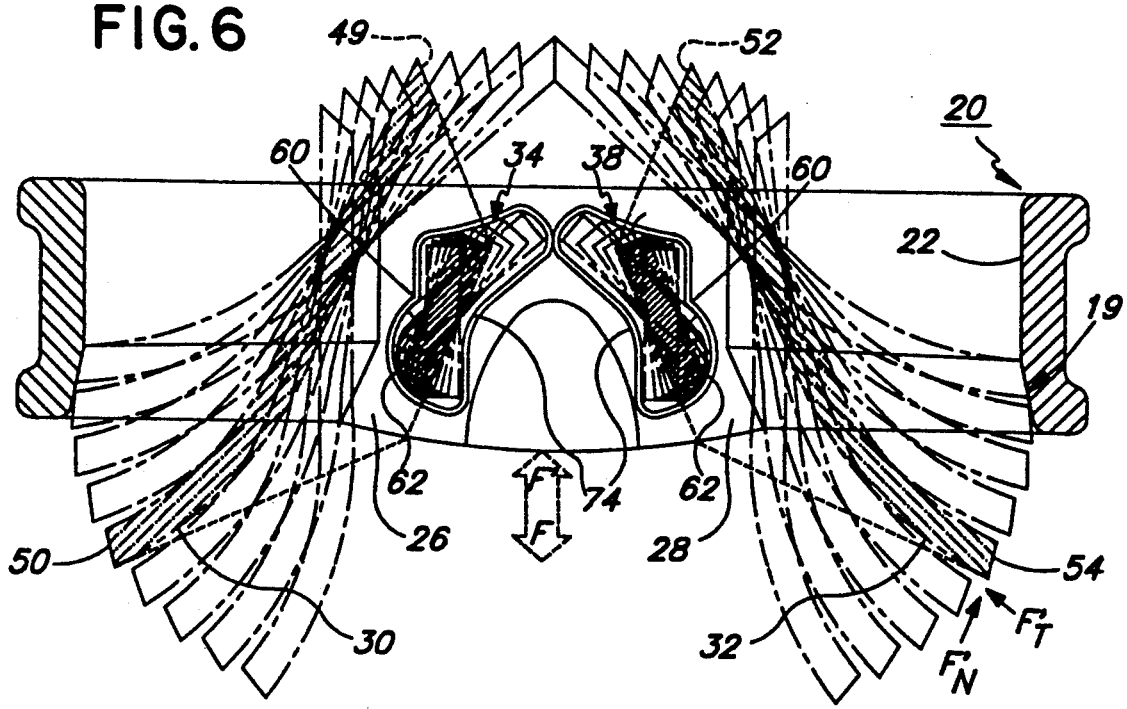
FIG. 6 is a cross-sectional view of the embodiment of the present invention illustrated in FIG. 2 taken along lines A—A of FIG. 2 with the valve leaflets intermediate the open position and closed position.
Figure 7:
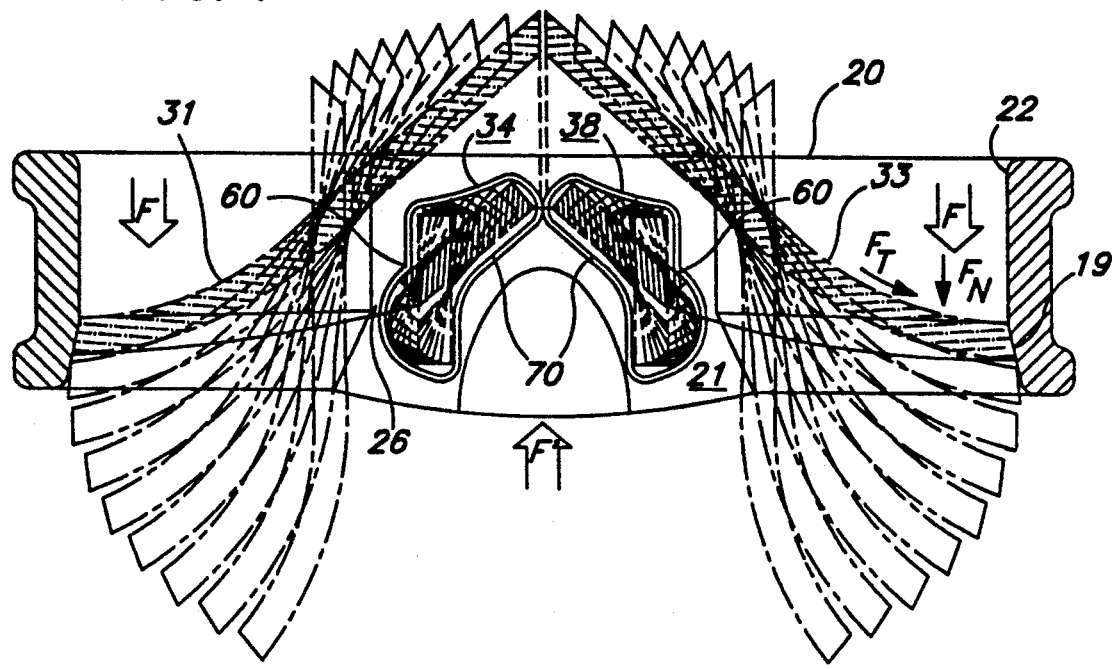
FIG. 7 is a cross-sectional view of the embodiment of the present invention illustrated in FIG. 2 taken along lines A—A of FIG. 2 with the valve leaflets in the closed position.

Referring now to the hinge mechanisms of the present invention viewed in FIGS. 2 and in part in FIGS. 3–7, they preferably include the leaflet ears 42, 44 of leaflet 26 and 46, 48 of leaflet 28 which are positioned within recesses 34, 36 and 38, 40, respectively. The recesses 34, 36, 38, 40 preferably have a generally flat bottom 58 bounded by curved side walls which curve concavely up from the flat bottom 58 to the flat surfaces 21, 23 to receive elongated ears 42, 44 and 52, 54 in a fashion as depicted in FIGS. 4A and 4B. FIGS. 5–7 specifically depict hinge recesses 34 and 38, although it will be understood that such hinge recesses are fashioned into flat surface 23 at 36 and 40 shown in FIG. 2.

As described earlier and as shown in FIG. 4B, each of the recesses 34, 36, 38, and 40 have a flat bottom and curved side and end walls which receive the leaflet ears which are also curved so that they present no abrupt or acute angles or edges subject to fracture or being worn as the leaflet ears traverse the recess.

In reference to FIG. 4A, it depicts the general outline of the hinge mechanism recess 34 or 40 (as well as the mirror image of the recesses 36 and 38) of FIG. 2 in relation to nine possible contact areas ("footprints") of an ear as the leaflet moves from the open position of FIG. 5 to the closed position of FIG. 7. In reference to FIGS. 5–7, nine successive positions of the leaflets 26 and 28 are shown corresponding to the footprints depicted in FIG. 4A.

Turning to FIG. 4B, it depicts a projection of the outline of the recess of FIG. 4A and a leaflet ear resting in the closed position corresponding to footprint F1 in FIG. 4A. The leaflet ear may, for example, be ear 42 of leaflet 26 resting in recess 34 of flat surface 21. FIG. 4B depicts a generally flat recess bottom surface 58 against which the generally flat surface of the ear 42 rests. The ear 42 is also shown as including relatively rounded ends and corners which bear against the generally curved side walls of recess 34. In this fashion, the ends of the elongated ears bear against the concave curved walls and the flat bottom of the recess 38 in pivoting through translational, rotational and translational movement back and forth between the open and closed positions.

Returning to FIG. 4A, the outline of the modified serpentine-epicycloid curve hinge recess is also shown in relation to the mathematical functions of FIGS. 4C, 4D and 4E which are used to generate the shape and in relation to the direction of downstream blood flow F (open leaflet position) and back flow F′ (closed leaflet position). Each hinge recess 34, 36, 38 and 40 includes the generally flat inner surface 58 and a pivoting edge or torque cam 60 that a side wall of the leaflet ears 42, 44, 46 and 48 bears against in the movement of the leaflets between the open position in FIG. 5 to the closed position in FIG. 7. The pivoting edge or torque cam 60 is defined by one epicycloid curved wall 62 and a flat wall 64 and curved wall 66 which are referred to as a serpentine curved wall. On the opposite side of each recess, the walls 72 and 70 meet at second pivoting edge or torque cam 74 against which the opposite side of the leaflet ears bear against in moving from the closed to the open position. It will be understood that each side edge of the leaflet ears may also be curved inward toward the flat inner surface 58 and that the torque cams 60 and 74 are curved in the same fashion as the other side walls 62, 64, 66, 70 and 72 between the surface of the flats 21 and 23 to the flat surfaces 58.

Referring now to FIGS. 4C to 4E, the epicycloid curve which shapes the wall 62 is generated as shown in FIG. 4D Similarly the modified serpentine shape of walls 64 and 66 is developed in accordance with the FIG. 4E projection from FIG. 4C.

Turning now to FIGS. 5–7, the leaflets 26 and 28 and elongated ears 42 and 46 are depicted in sectional views taken along the lines A—A from the top view depicted in FIG. 2. A set of nine possible positions extending between the fully open position of FIG. 5 and the fully closed position of FIG. 7 are depicted in the phantom lines. The general outlines of the valve leaflets are depicted in dotted lines connecting the minor and major edges 49, 50 and 52, 54, respectively, of the two valve leaflets and the leaflet ear in the solid line position in each respective figure.

The recesses 34 and 38 depicted in FIGS. 5–7 are cut into a flat 21 on inner wall 22. Similarly, a flat 23 (as shown in FIG. 2) on the opposite side of the inner surface 22 of annular valve base 20 bears the hinge mechanism recesses 36 and 40. The annular valve base 20 also includes a valve seating surface 19 which constitutes about a 15° surface cut from inner surface 22 and extending between the flats 21 and 23 (FIG. 2).

In the fully open position of the valve leaflets depicted in FIG. 5, the leaflet surfaces over a major portion of each leaflet is parallel to the direction of downstream blood flow depicted by the arrow labeled F. Similarly, the ears 42 and 46 are depicted parallel to the direction of blood flow and bear against the flat walls 64 and 72 of the recesses 34 and 38. The curvature of the trailing portion of the outer surfaces 31, 33 of leaflets 26, 28, respectively, approaching the major edges 50, 54 provides reduced boundary layer separation and reduces wake regions and turbulence downstream of the major edges 50, 54. The tangential flow of blood between the outer surfaces 31, 33 and the inner surface 22 of the valve body 20 washes those surfaces. At the same time, the flat inner surface 58 and the walls of the recesses 34, 38 are washed by blood except in the position occupied by the leaflet ears 42, 46.

If the valve depicted in FIGS. 5–7 is implanted as an aortic replacement, then the direction of blood flow F depicted in FIG. 5 is attained on the pumping stroke of the heart, as a respective ventricle contracts. Pivoting movement in the direction of blood flow F is stopped on contact of the opposite edges of the ears 42 and 46 (and 44, 48) against the flat recess surfaces 64 and 72 of each recess 34, 38 (and 36, 40).

When, at the end of a ventricular stroke, the respective ventricle relaxes to draw more blood into the chamber from the atrium, the back pressure (represented by the arrows $F'$, $F'_N$, $F'_T$) within the aorta causes the leaflets 26, 28 to quickly swing or pivot to the closed position depicted in FIG. 7. In FIG. 6, the leading edge of the elongated ears 42 and 46 is shown bearing against the serpentine walls 66 of recesses 34 and 38 and against the concave epicycloid wall 62. Continued blood flow in the direction $F'$ will, through the application of tangential force $F'_T$ along the inner surfaces 30 and 32, cause the valve leaflets to continue to rotate and translate to the fully closed position depicted in FIG. 7. As the valve leaflets begin to close, the tangential forces $F'_T$ and normal forces $F'_N$ applied against the inner surfaces 30 and 32 (shown in both FIGS. 5 and 6) rapidly accelerate the minor edges 48 and 52 of the valve leaflets toward one another. But in doing so, the cosine value of tangential force $F'_T$ reduces, and the normal force $F'_N$ applied to the full exposed inner surface 30 and 32 tends to increase. The serpentine walls 66 of recesses 34, 38 guide the movement of the leading edge of the leaflet ears, and thus the movement of the entire leaflet. Therefore, the speed at which the leaflets pivot toward one another first accelerates and then decelerates. Consequently, the closing speed of the leaflets in the phantom line positions between the intermediate position depicted in FIG. 6 and the fully closed position depicted in FIG. 7, decelerate. The deceleration allows the trapped blood between the converging minor edges 48, 52 and the major edges 50, 54 and the seat 19 to escape being crushed.

Turning now to FIG. 7, the leaflets 26 and 28 and leaflet ears 42 and 46 are shown in the fully closed position. In viewing FIGS. 5–7 together, the successive rotation and translation of the valve leaflets 26 and 28 can be visualized. It can also be seen, that as the leaflet ears rotate and translate across the flat surfaces 58 of the hinge mechanism recesses, each opening and closing phase of the valve leaflets wipes the surface 58 as well as the walls defining the shape of the recess clean of blood cells. This wiping action reduces blood clotting in the vicinity of the hinge mechanism.

Turning now to the opening phase of the valve leaflets, for example upon the next pumping stroke of the heart, blood pressure applied (as shown in FIGS. 7 and 6) in the downstream flow direction F against the leaflet outer surfaces 31 and 33 causes the leaflets 26 and 28 to pivot open rapidly because of the significant effect of the hinge mechanism toward the center of the valve body 20. Again, the valve leaflets 26, 28 rapidly accelerate in both rotation and translation to the intermediate point depicted in FIG. 6. As blood begins to flow in the direction F through the central orifice, the normal force $F_N$ against the outer surfaces 31 and 33 of the leaflets begins to decrease and the leaflets 26, 28 decelerate as they rotate and translate toward the fully open position of FIG. 5.

Although FIG. 6 specifically depicts the rotation and translation of the leaflets and the leaflet ears against cam 60 and serpentine wall 66 as blood flow reverses direction from the downstream direction depicted in FIG. 5, it may be imagined as illustrating an intermediate position which may be attained in the opening phase of the leaflets by translating the ear to bear against the cam 74 and epicycloid surface 62. The rapid acceleration and deceleration of the valve leaflets as they move from the open to closed and closed to open positions effectively use the dynamic normal and tangential forces to decrease closing velocity of and consequently increase fatigue life of the valve leaflets at the major and minor edges and at the hinge mechanisms. Particularly, in the closing of the valve leaflets, the deceleration decreases leaflet landing or contact velocity and any tendency of the major edges 50, 54 to stick by impacting the annular seat 19. In addition to reducing leaflet impingement tendency, the deceleration and low leaflet landing velocity provide a low closing noise and reduce hemolysis of trapped blood cells. The acceleration and deceleration thus minimize damage to the blood and reduce wear of the leaflets and annoying noise to the patient.

Turning now to FIGS. 8 and 9, perspective views of the valve leaflets 26, 28 and annular base 20 are presented for purposes of illustration. FIG. 9 in conjunction with FIG. 7 shows that the overall profile of the valve in the closed position is relatively low and is unlikely to interfere with any cardiac structure in the desired positions of implantation. FIG. 8, viewed in conjunction with FIGS. 2 and 5, shows the relatively large central orifice with respect to the side orifices of the present invention.

Figure 10:
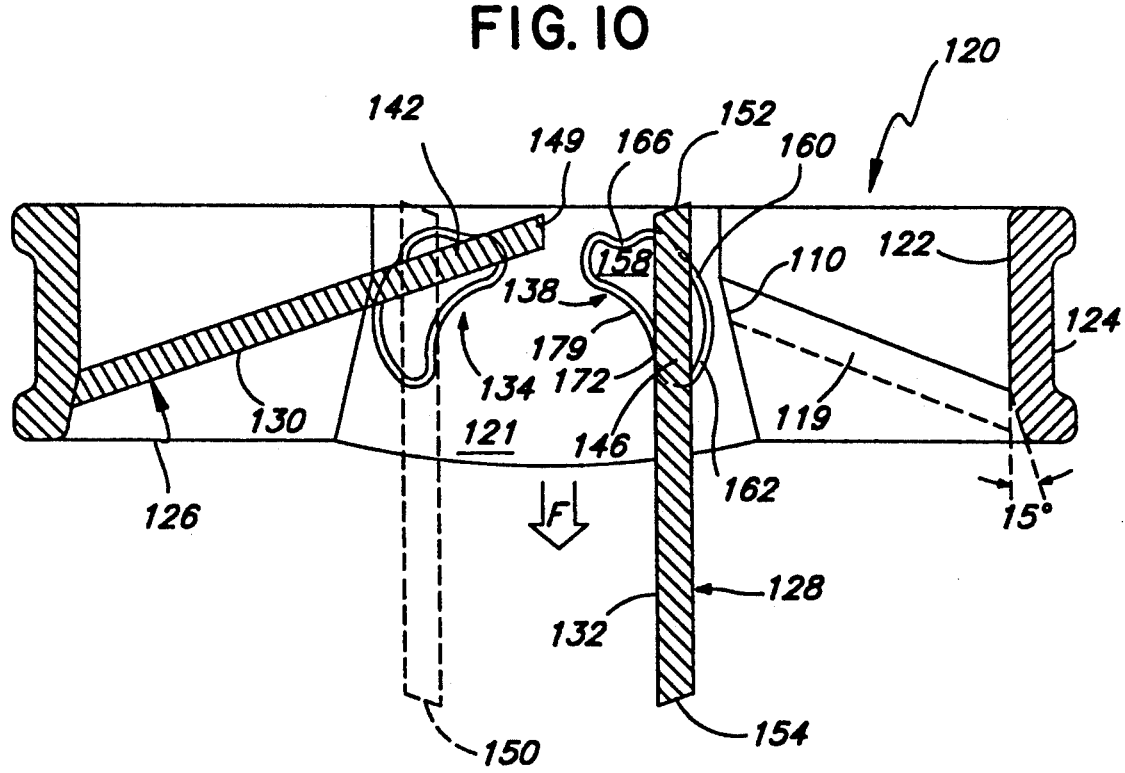
FIG. 10 is a cross-sectional view of a further embodiment of the present invention employing flat valve leaflets in conjunction with a modified serpentine-epicycloid curve hinge recess and elongated leaflet ears.

Turning now to FIG. 10, it depicts in cross-section a bileaflet prosthetic heart valve having a pair of flat leaflets 126, 128 mounted within the annular base 120 where the leaflet 126 is depicted in solid lines in the fully closed position and in dotted lines in the fully open position and the leaflet 128 is depicted in the fully open position. The embodiment of FIG. 10 employs the modified serpentine-epicycloid hinge recess depicted in FIG. 4A to 4E and the other figures of the first embodiment of FIGS. 2–9. For ease of description, elements which by correspondence or similarity in the first embodiment are enumerated in a similar fashion.

In the FIG. 10 embodiment, it will be understood that the FIG. 4E depiction of the leaflet ears to the hinge recesses applies. Similarly, the description of the generation of the modified serpentine-epicycloid curve hinge recess outline and concave curve sidewalls also applies. In a similar fashion, as described above, the valve leaflet ears are guided by the recess shape and camming points to provide translational, rotational and translational movement in moving between the open and closed positions. The valve leaflets 126, 128 and leaflet ears 142, 146 may be of the general configuration depicted in the above-listed U.S. Pat. No. 4,689,046, incorporated herein by reference.

One aspect of the FIG. 10 embodiment relating to the angle of the valve seat 119 is that the major leaflet edges 150, 154 bear against in the closed position. In FIG. 10, the valve seat is an angular cut in the inner surface 122 at an angle of about 15° at a point equidistant from the flat surfaces 121, 123 and decreasing to about 11° where the seat 119 meets the flat surface 121, 123 this change in the angular cut into the surface 122 is necessary because of the oblique angle that the valve leaflets assume when in the closed position as depicted by leaflet 126 in FIG. 10. Although not specifically shown, it will be understood that the arcuate edges 150, 154 are similarly cut at 11° adjacent to the point where the leaflet ears protrude from the sides of the leaflets to 15° at the point depicted in FIG. 10 where the major arcuate edges are equidistant from the leaflet ears. In this fashion, separate valve seats 119 are provided for each of the leaflets 126 and 128, both seats being cut into the inner surface 122 of the annular base 120 to accommodate the valve leaflets 126, 128 without allowing backflow leakage of blood or impingement of the leaflets in the closed positions.

One of the advantages of the embodiment in FIG. 10 is that the leaflets in the fully open position are fully parallel with blood flow F. The reversal of blood flow in tangential forces acting on the inner and outer surfaces of the leaflets 126 and 128 will cause the leaflet ears to translate and bear against the serpentine curved sidewalls of the hinge recesses causing the leaflets to rotate toward the closed position, whereupon normal backflow force F' applied to the inner surfaces 130 and 132 accelerate the closure. Upon reaching a point in the closure approaching the fully closed position, the serpentine curvature again causes the leaflets to translate toward one another and toward the central axis of the annular base 120 while decelerating. In this fashion, the flat leaflet embodiment employing the modified serpentine-epicycloid curve hinge recesses and elongated leaflet ears provides all of the benefits described above except that the blood flow volume is more equally distributed between the central orifice and the side orifices.

Returning now to FIGS. 11A and 11B, the approximate acceleration and deceleration characteristics of the heart valve of FIG. 1 and the embodiment of the present invention are depicted, respectively. The tangential velocity $V_t$ over the time $t_o-t_c$ that it takes for the leaflets to pivot between the open and closed positions are depicted. The characteristics of the FIG. 1 prior art heart valve are derived from the publication entitled "The Closing Velocity of Baxter Duromedic Heart Valve Prostheses," by G. X. Guo et al, *ASAIO Transactions*, 1990; 36:M529–M532, and in particular from the velocity data contained therein. The characteristics depicted in FIG. 11B illustrate the effects of the translation, rotation and translation depicted in FIGS. 5–7 and 10 in conjunction with the normal and tangential forces exerted by the blood flow. The cooperation of the torque cams and the modified epicycloid-serpentine guide walls of the elongated hinge recesses provide the advantage of the rapid acceleration and deceleration depicted in FIG. 11B and the consequent advantages of low closing noise, increased fatigue life, reduced fracture tendency of components, decrease in the possibility of cavitation at the trailing, major edges of the leaflets, full washing of the recessed surfaces and walls and the effective use of the dynamic forces to reduce leaflet impingement tendency and damage to blood cells. In regard to impingement, it should be understood that physicians on occasion loop sutures through the valve body orifice when affixing the valve in place and high velocity closure may cause the leaflet to stick against the suture and fail to open again as a result. The relationship of the angle of the seat 19 to the inner wall 22 of the base 20 and the angle of the downstream or major leaflet edges 50, 54 to the seat 19 angle, together with decreasing closure velocity of the major edges 50, 54 to seat 19, reduces the tendency of impingement, even if suture is placed through the orifice during implantation.

FIGS. 12–15 illustrate a third embodiment of a heart valve according to the present invention. In this embodiment, the epicycloid guide walls associated with the hinge recesses of the above embodiments are replaced by straight guide walls oriented perpendicular to the plane defined by the lower (outflow) surface of the valve base, while the serpentine guide walls are retained. The leaflets employed in this embodiment are leaflets having a compound curvature similar to that employed in the valve illustrated in FIG. 2. As will be discussed below, the change in recess configuration as compared to the recesses employed in the embodiment illustrated in FIG. 2 results in a leaflet movement which comprises an initial, rapid rotation at the beginning of both the closing phase and the opening phase, with motion changing thereafter to combined rotation and translation and thereafter to translation. As in conjunction with the embodiments illustrated above, the change from rotation to translation as part of the closing movement results in a reduction in impact force at the point of closing. The substitution of the straight for the epicycloid guidewall also provides a reduction in dynamic regurgitation during the closing phase and improved efficiency during the opening phase.

FIG. 12 illustrates the valve base 200 used in this third embodiment of the present invention. The base is provided with a flared outflow of section 202, which defines an angle of about 10° with respect to the cylindrical inner wall 203. Hinge recesses 204 and 206 are located in flat wall 208. Corresponding hinge recesses are located diametrically across the valve base 200 as indicated generally at 209, in a fashion similar to the valve bases illustrated in the above figures.

Figure 13:
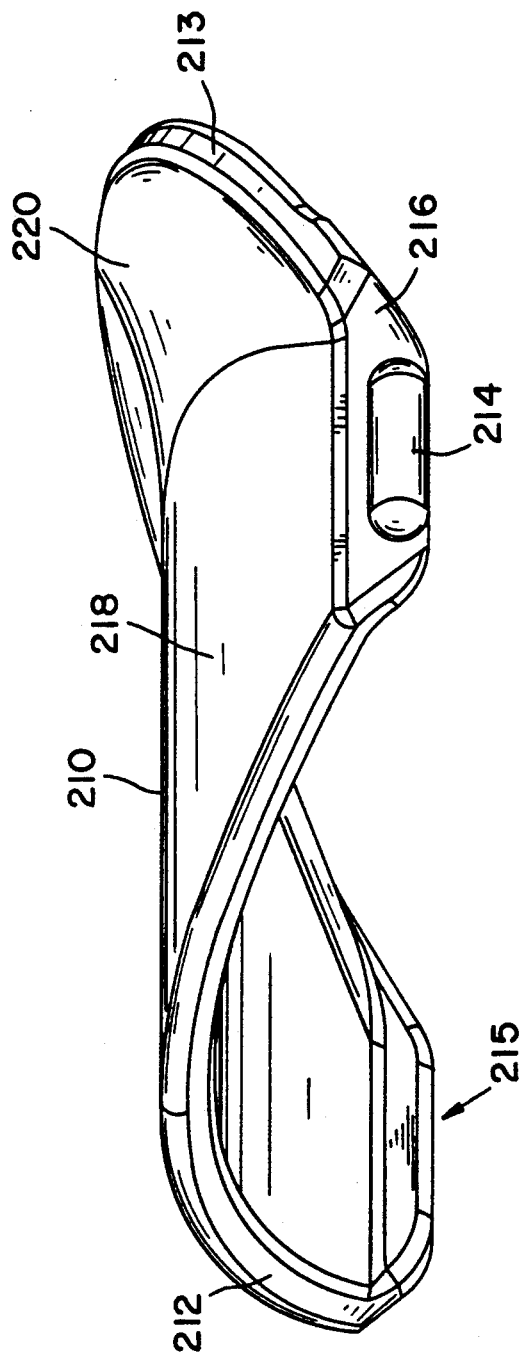
FIG. 13 is a perspective view of a valve leaflet of a further embodiment of the present invention for use in conjunction with the housing illustrated in FIG. 12.

FIG. 13 is a perspective view of a valve leaflet 210. The assembled valve, like those illustrated in the Figures above, employs two such leaflets. The overall configuration of the leaflet is likewise similar to those described in conjunction with the figures above. The leaflet possesses a complex shape including an arcuate major edge 213 which sealingly contacts the flared outflow section 202 of the valve body 200, an arcuate minor edge 212, which sealingly contacts the corresponding minor edge on a corresponding second leaflet, when the leaflets are in the closed position and two side edges 215, 216, which carry projections or ears which are located in the hinge recesses when the valve is assembled.

Like the leaflets illustrated above, leaflet 210 includes a first portion 218 which generally takes the form of a portion of the surface of the circular cylinder. The valve leaflet also includes a second portion 220, continuing the curvature of the cylindrical section 218, but also curved about 3 degrees around a radius of curvature transverse to the arc of curvature of the cylindrical portion 218. The composite structure thus resembles a saddle in overall form. The leaflet as illustrated of approximately uniform thickness, with inflow and outflow surfaces of the leaflet being generally parallel. On each side edge of the leaflet there is a flattened surface and a projection for engaging with a corresponding recess on the valve body. In this view, only one flattened edge surface 216 and one projection 214 are visible. However, as in the leaflets illustrated above, a second, corresponding flattened surface and projection are located diametrically across the valve leaflet at the opposite side edge 215. The projection 214 differs somewhat from those illustrated in the leaflets above in that it takes the form of a cylindrical surface, provided with spherical end surfaces.

Figure 14:
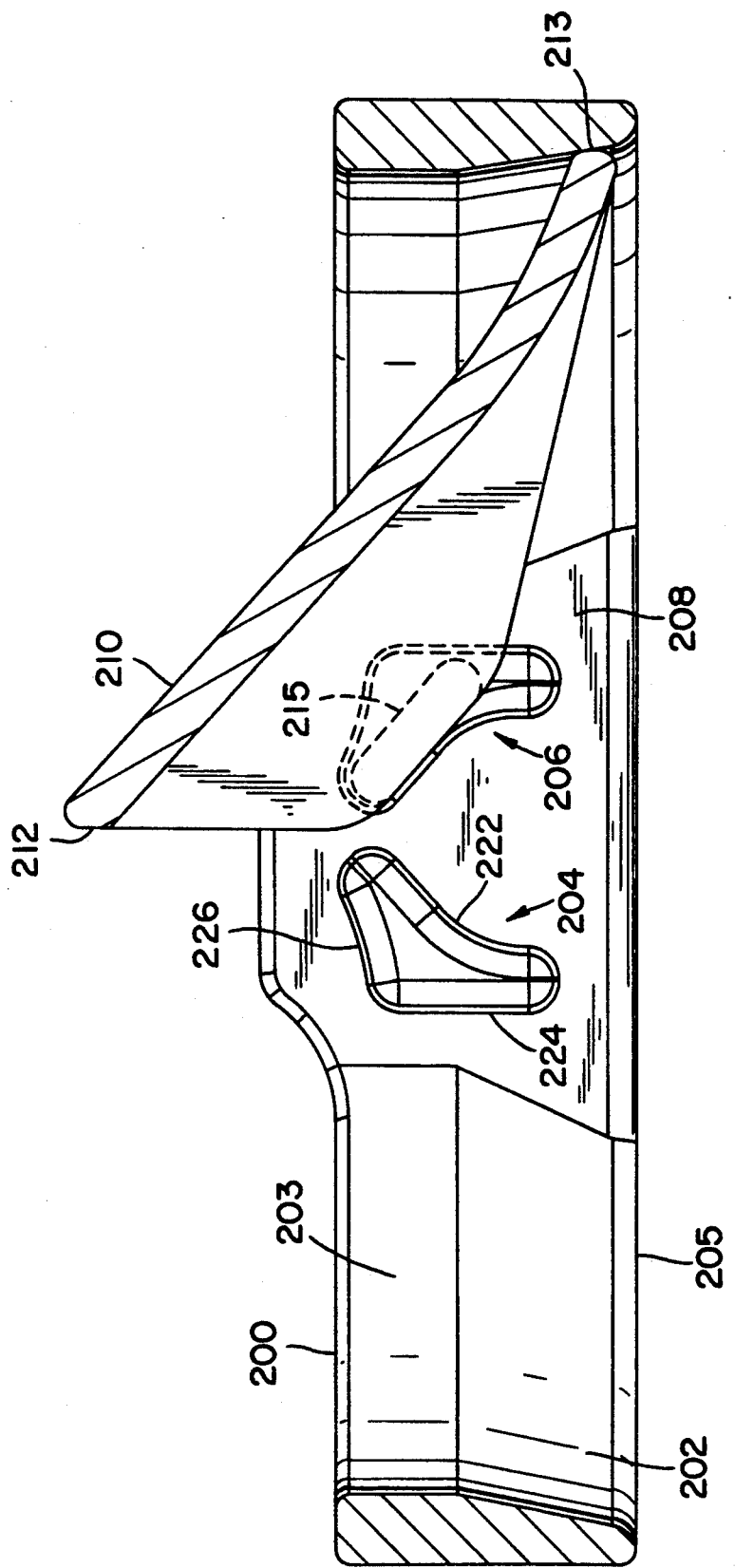
FIG. 14 is a cross sectional view of a further embodiment of a valve according to the present invention employing the housing and leaflets of FIGS. 12 and 13, illustrating one leaflet in the closed position.

FIG. 14 is a cross-sectional view through the valve, illustrating one of the two leaflets, in cross-section, and illustrating the hinge recesses in more detail. As can be seen in this view, each hinge recesses includes a serpentine guide wall 226, a generally straight guide wall 224 and a wall 222 that defines a cam surface. In addition to the difference in overall configuration, the recesses of this embodiment of the valve differ from those illustrated above in that the recess walls take the form of internal cylindrical or spherical surfaces, of the sort that might be produced by means of a rotary grinder, and are also provided with a slight bevel, around the periphery of the walls, at the point they join the flat surface 208. The radius of the cylindrical and spherical wall sections surrounding the recesses is approximately equal to or slightly larger than the radius of the cylindrical and spherical surfaces which make up the corresponding projections or ears on the valve leaflets.

As illustrated in FIG. 14, in the closed position, major edge 213 seals against the tapered outflow wall 202, with minor edge 212 positioned so that, in the presence of a second leaflet, it would be adjacent the corresponding minor edge of the adjacent leaflet. In FIG. 14, the outline of the leaflet projection or ear 215 is visible, illustrating its location when the leaflet is in the closed position.

Figure 15:
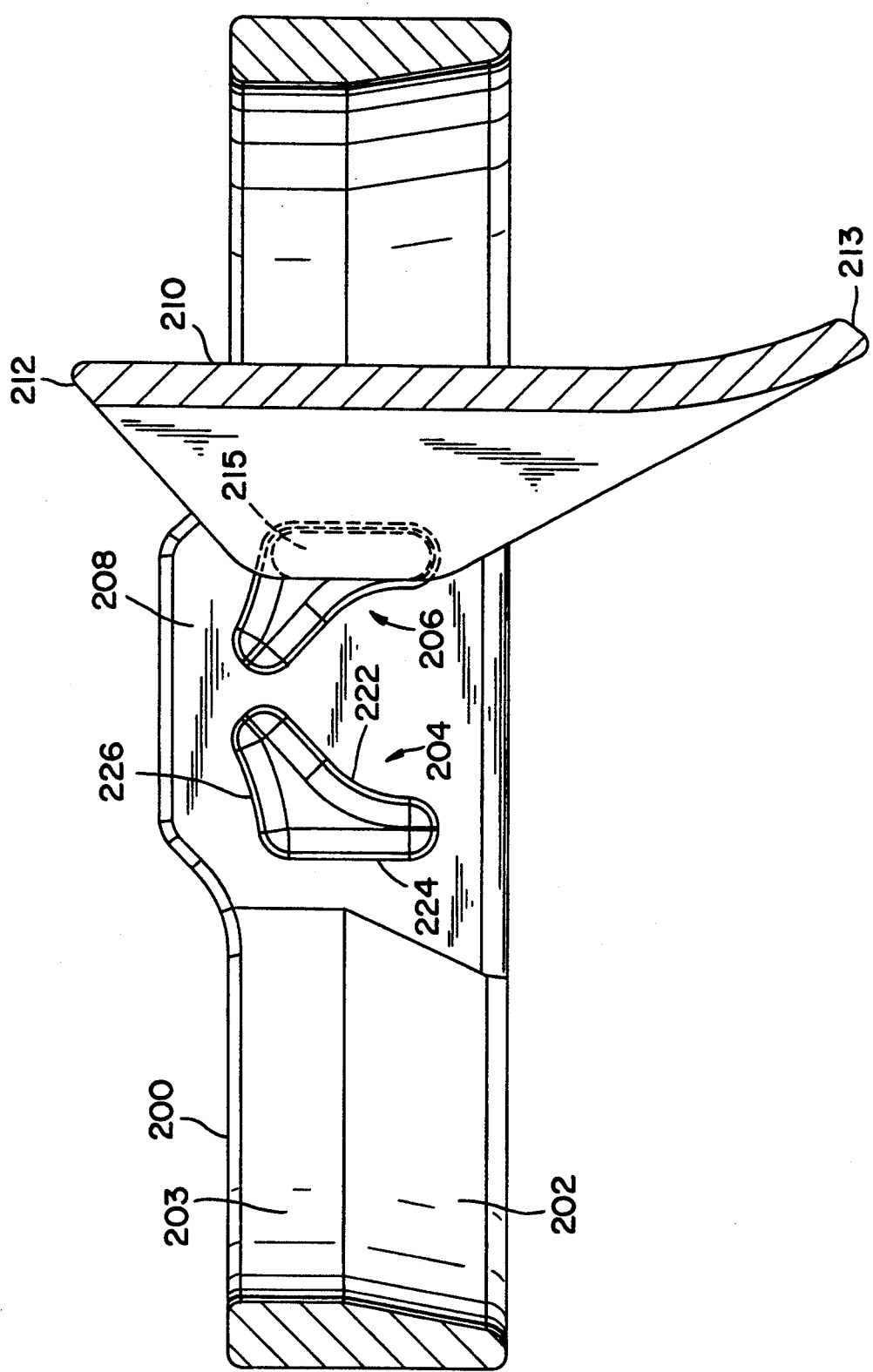
FIG. 15 is a cross sectional view of a further embodiment of a valve according to the present invention employing the housing and leaflets of FIGS. 12 and 13, illustrating one leaflet in the open position.

FIG. 15 illustrates the same valve, from the same view as illustrated in FIG. 14, but shows the leaflet in the open position, with the projection 215 lying adjacent the straight guide wall of recess 206. As can be seen in the open position, the cylindrical portion 218 of the leaflet is located parallel to the directional flow through the valve base, parallel to cylindrical wall 203 and perpendicular to the lower (outflow) surface 205 of valve base 200, with the curved or flared portion 220 of the leaflet located downstream of the valve base with the leaflet in open position.

In general, the valve of FIGS. 12-15 functions in a fashion similar to that of the valves illustrated in FIGS. 1-11 above. However, the substitution of the straight guide walls for the epicycloid guide walls has significant consequences, and provides enhanced valve performance. In particular, substitution of the straight guide wall (e.g., 224) for an epicycloid guidewall forces the leaflet to move quickly during the initial parts of the opening and closing phases. The result is that during opening and closing, the leaflet sequentially rotates, rotates and translates and finally translates into the open or closed position. The hinge design thus retains the desirable translation from rotational to transitional movement as part of the closing phase of valve operation, preserving the low impact closing forces at the contact surfaces between leaflets in the valve rings, provided by the hinge designs above. Increasing the speed of the valve during the initial phases of opening and closing improves opening efficiency and reduces regurgitation during the closing phase. The velocity of the leaflet is at its most rapid during the initial portions of both the opening and closing phase, with the velocity decaying as the leaflet changes motion from rotation to translation.

In the embodiment illustrated in FIGS. 12-15, the area between the leaflets in the open position constitutes approximately 50% of the orifice area of the valve housing. As a result, at least 70% of the blood flow will be through the central area, at full open position. In the valve as illustrated, the swing angle between full open and full close position is about 48°. The configuration of the valve leaflets, like those illustrated in FIGS. 2-11 above, results in a delayed flow boundary layer separation along the leaflet surface, reducing wake regions at the outflow side and thus reducing turbulence and eddy currents downstream of the leaflets. Therefore, like the designs illustrated in FIGS. 2-11 above, red blood cell and platelet damage due to turbulence should be minimal.

The annular valve base and the leaflets of the mechanical heart valve prosthesis embodiments of the present invention are preferably made entirely of pyrolytic carbon in accordance with processes which are known in the art. As is known, pyrolytic carbon material has very little thrombogenecity and is generally considered safe for use in mechanical heart valve prosthesis.

What has been described above are improved mechanical heart valve prostheses which are relatively simple to construct and which minimize the possibility for stagnation of blood flow and formation of incipient blood clots. Furthermore, the composite curvature of the leaflets of the first and third embodiments provides maximal flow through the central orifice defined by the leaflets in their open phase and provides consequent lower pressure drop with the leaflets parallel to the flow stream during the open phase. The curved leaflet major or trailing edges in the open phase reduce boundary separation and associated turbulence along the flow stream direction.

In all embodiments, the passage of blood through the central orifice and the two peripheral or side orifices between the outer valve leaflet surfaces and the annular valve base inner surface washes both sides of the leaflets and the hinge mechanism. The shapes of the hinge recesses and elongated leaflet ears provide acceleration and deceleration during the movement of the valve leaflets between the open and closed positions in order to minimize damage to blood cells, wear of the valve leaflets and hinge components, impingement, and annoying noise to the patient.

Modifications to the mechanical heart valve prosthesis of the present invention may become readily apparent to those skilled in the art in light of the foregoing disclosure. Therefore, the scope of the present invention should be interpreted solely from the following claims, as such claims are read in light of the disclosure.

What is claimed is:

1. A heart valve prosthesis comprising:
   a generally annular valve base having an interior surface which defines a central passageway for blood flow in a downstream direction and a pair of leaflets mounted therein; and
   hinge means for supporting said pair of leaflets for substantially pivoting movements on eccentric axes between a closed position generally blocking blood flow through said central passageway and an open position allowing blood flow therethrough in said downstream direction;
   wherein each of said pair of valve leaflets has a first arcuate major edge which is configured to interface with the interior surface of said annular base in a blood flow sealing relationship therewith and a second, minor edge which is configured to interact with the said second minor edge of the other leaflet in a fluid flow sealing relationship therewith when in a closed position, each of said leaflets further having opposite and generally parallel inflow and outflow surfaces, wherein said inflow and outflow surfaces are curved to define generally cylindrical surfaces in regions of said leaflets adjacent said minor edges and said inflow and outflow surfaces are curved in along a second radius of curvature in the regions of said leaflets adjacent said major edges, said second radius of curvature being generally transverse to the curvature of said cylindrical surfaces and located downstream of said valve base when said leaflets are in their open position.

2. A heart valve prosthesis comprising:
   a generally annular valve base having an interior surface which defines a central passageway for blood flow in a downstream direction and a pair of leaflets mounted therein; and
   hinge means for supporting said pair of leaflets for substantially pivoting movements on eccentric axes between a closed position generally blocking blood flow through said central passageway and an open position allowing blood flow therethrough in said downstream direction;
   wherein each of said pair of valve leaflets has a first arcuate major edge which is configured to interface with the interior surface of said annular base in a blood flow sealing relationship therewith and a second, minor edge which is configured to interact with the said second minor edge of the other leaflet in a fluid flow sealing relationship therewith when in a closed position, each of said leaflets further having opposite and generally parallel inflow and outflow surfaces, wherein said inflow and outflow surfaces are curved to define generally cylindrical surfaces in regions of said leaflets adjacent said minor edges and said inflow and outflow surfaces are curved in along a second radius of curvature in the regions of said leaflets adjacent said major edges, said second radius of curvature being generally transverse to the curvature of said cylindrical surfaces and located downstream of said valve base when said leaflets are in their open position and oriented such that on each of said leaflets, said inflow and outflow surfaces in said regions adjacent said major edges are curved along said second radius of curvature outwardly away from the other of said leaflets.

3. The heart valve prosthesis of claim 1 or claim 2 wherein said hinge means further comprises:
   two pairs of recesses positioned within the interior surface of said annular base and having recess walls defining camming means; and
   a pair of ears projecting from opposite side portions of each said leaflet and adapted to be fitted within a respective pair of said recesses.

4. The heart valve prosthesis of claim 3 wherein said ears are shaped to fit within said recesses in an open position whereby a portion of said inner and outer surfaces of said valve leaflets extending from said minor edge, in each leaflet, is generally parallel with downstream direction blood flow through said central passageway defined by said annular base interior surface and said inner and outer leaflet surfaces.

5. The heart valve prosthesis of claim 1 or claim 2 wherein said hinge means and the curvature of the inner and outer surfaces of said valve leaflets provide a ratio of volumetric blood flow through the central passageway defined by a spatial volume between said facing inner surfaces of said valve leaflets in said open position and a total unobstructed passageway volume within said interior surface of said annular base in said open position that is equal to or greater than 70%.

6. The heart valve prosthesis of claim 3 wherein said hinge means and the curvature of the inner and outer surfaces of said valve leaflets provide a ratio of volumetric blood flow through the central passageway defined by a spatial volume between said facing inner surfaces of said valve leaflets in said open position and a total unobstructed passageway volume within said interior surface of said annular base in said open position that is equal to or greater than 70%.

7. The heart valve prosthesis of claim 4 wherein said hinge means and the curvature of the inner and outer surfaces of said valve leaflets provide a ratio of volumetric blood flow through the central passageway defined by a spatial volume between said facing inner surfaces of said valve leaflets in said open position and a total unobstructed passageway volume within said interior surface of said annular base in said open position that is equal to or greater than 70%.

8. A heart valve prosthesis comprising:
   a generally annular valve body having an interior surface defining a central passageway designed to be implanted to permit blood flow therethrough in a downstream direction and defining a valve leaflet seat;
   a pair of valve leaflets which are supported for substantially pivotal movement on eccentric axes between a closed position generally blocking blood flow through said central passageway and an open position allowing blood flow therethrough in said downstream direction,
   said leaflets and said valve body including projecting ears and recesses, respectively, which receive said ears, said projecting ears and said recesses having complementary surfaces which mount said leaflets in a manner to allow pivotal movement relative to sand annular valve body;
   said recesses being elongated so that there is sequential rotational and translational movement of said ears within said recesses as said leaflets pivot between the open position and the closed position, and being formed in said interior surface at generally diametrically opposite locations wherein said ears are received;

each of said elongated recesses having a transverse dimension and extending for a longitudinal distance greater than its transverse dimension and having a modified serpentine curved guide wall extending toward one end of the elongated recess and a second guide wall extending toward the other end of said elongated recess, said guide walls oriented so that said ears move back and forth there along at the same time said ears move rotationally thereagainst, thereby defining a shifting pivot axis relative to said valve body as said leaflets pivot in each direction between the closed and open positions.

9. A heart valve in accordance with claim 8 wherein said leaflets are curved in cross section between said projecting ears having convex outer surfaces facing upstream and concave inner surfaces facing downstream when in the closed position.

10. The heart valve prosthesis of claim 8 wherein said leaflet ears are configured to bear against said serpentine curved guide walls in rotational and translational movement of said leaflets from said open to said closed position.

11. The heart valve of claim 9 wherein said leaflets each have an arcuate major edge which is configured to interface with said interior surface of said annular valve body in a generally blood flow sealing relationship therewith when in said closed position and a second, minor edge which is configured to interact with the other minor edge of the other leaflet in a generally fluid flow sealing relationship therewith.

12. A heart valve prosthesis comprising:
a generally annular base having an interior surface forming a central passageway therethrough of generally circular cross section for blood flow in a downstream direction; said base defining valve seat means;
a pair of valve leaflets proportioned to block blood flow downstream through said passageway when said leaflets are disposed in a closed position;
each of said leaflets having an arcuate major edge which abuts said valve body seat means and a minor edge which abuts the said minor edge of the other leaflet in said closed position;
means for pivotally interconnecting each of said leaflets and said valve body for relative pivotal movement between the closed position and an open position wherein said arcuate major edges are situated in the blood flow downstream, which interconnecting means includes pairs of recesses formed in generally opposite locations in said interior wall and pairs of ears extending laterally from each of said leaflets;
each recess in a said pair of recesses having a downstream section which is aligned substantially parallel to the centerline of said central passageway and an upstream section which connects at a point of connection to said downstream section and angles toward the other said recess in said pair of recesses from the point of connection of the sections and wherein said recess upstream sections each have a first curved shape defined by a first wall section and said recess downstream sections each have a shape defined by a second wall; and
wherein said ears are configured with respect to said first and second curved shapes and wall such that, upon the beginning of backflow, said leaflet ears first rotate about said point of connection and then decelerate and translate as normal forces of upstream blood flow direct said leaflet ears against said point of connection and toward the end of said upstream section.

13. The heart valve prosthesis of claim 12 wherein said leaflet ears and said recess sections are configured to provide an angular rotation of said leaflets between said open and said closed position of about 50 degrees.

* * * * *